United States Patent
Stewart et al.

(10) Patent No.: US 10,452,815 B2
(45) Date of Patent: Oct. 22, 2019

(54) CONTROL SYSTEM FOR CONTROL OF DISTRIBUTION OF MEDICATION

(71) Applicant: ZOGENIX INTERNATIONAL LIMITED, Berkshire (GB)

(72) Inventors: Richard Alistair Balfour Stewart, Henley-on-Thames (GB); Anthony Clarke, Berkshire (GB)

(73) Assignee: Zogenix International Limited, Berkshire (GB)

( * ) Notice: Subject to any disclaimer, the term of this patent is extended or adjusted under 35 U.S.C. 154(b) by 1005 days.

(21) Appl. No.: 14/867,862

(22) Filed: Sep. 28, 2015

(65) Prior Publication Data
US 2016/0092652 A1 Mar. 31, 2016

Related U.S. Application Data

(60) Provisional application No. 62/056,836, filed on Sep. 29, 2014.

(51) Int. Cl.
*G06F 19/00* (2018.01)
*G06F 17/30* (2006.01)
(Continued)

(52) U.S. Cl.
CPC .... *G06F 19/3462* (2013.01); *G06F 16/24573* (2019.01); *G06F 19/3456* (2013.01); *G16H 10/60* (2018.01)

(58) Field of Classification Search
USPC .......................................................... 705/2–4
See application file for complete search history.

(56) References Cited

U.S. PATENT DOCUMENTS 3,117,160 A 1/1964 Holland
3,198,833 A 8/1965 Beregi
(Continued)

FOREIGN PATENT DOCUMENTS

EP 2 399 513 A1 12/2011
EP 3170807 5/2017
(Continued)

OTHER PUBLICATIONS

Boel et al. (Add-on therapy of fenfluramine, Neuropediatrics, 1996; available at https://www.thieme-connect.com/products/ejournals/pdf/10.1055/s-2007-973781.pdf.*
(Continued)

*Primary Examiner* — Mark Holcomb
(74) *Attorney, Agent, or Firm* — Karl Bozicevic; Bozicevic, Field & Francis LLP

(57) ABSTRACT

A system of controlling distribution of a medication in the treatment or prevention of epilepsy is provided. A central controller of the system has a data store and one or more processors for reading and writing data to the data store. The data store comprises a database of patient records, each patient record having a medication authorization field. The central controller can output an authorization of a first prescription of epilepsy medication to a patient in dependence upon genetic test results for the patient and schedules a subsequent test for the patient prior to authorization of a subsequent prescription of epilepsy medication. Also provided are methods in which the subject systems find use. The systems and methods find use in the treatment of severe subtypes of epilepsy or refractory epilepsy, such as Dravet Syndrome.

9 Claims, 6 Drawing Sheets

(51) Int. Cl.
 *G06F 16/2457* (2019.01)
 *G16H 10/60* (2018.01)

(56) References Cited

U.S. PATENT DOCUMENTS

| | | | |
|---|---|---|---|
| 3,759,979 | A | 9/1973 | Beregi et al. |
| 4,824,987 | A | 4/1989 | Kleemann et al. |
| 5,587,398 | A | 12/1996 | Elmaleh et al. |
| 5,808,156 | A | 9/1998 | Cannata et al. |
| 5,811,586 | A | 9/1998 | Cannata et al. |
| 6,045,501 | A | 4/2000 | Elsayed et al. |
| 6,315,720 | B1 | 11/2001 | Williams et al. |
| 6,561,976 | B2 | 5/2003 | Elsayed et al. |
| 6,561,977 | B2 | 5/2003 | Williams et al. |
| 6,755,784 | B2 | 6/2004 | Williams et al. |
| 6,869,399 | B2 | 3/2005 | Williams et al. |
| 6,908,432 | B2 | 6/2005 | Elsayed et al. |
| 7,141,018 | B2 | 11/2006 | Williams et al. |
| 7,668,730 | B2 | 2/2010 | Reardan et al. |
| 7,765,106 | B2 | 7/2010 | Reardan et al. |
| 7,765,107 | B2 | 7/2010 | Reardan et al. |
| 7,797,171 | B2 | 9/2010 | Reardan et al. |
| 7,874,984 | B2 | 1/2011 | Elsayed et al. |
| 7,895,059 | B2 | 2/2011 | Reardan et al. |
| 7,959,566 | B2 | 6/2011 | Williams et al. |
| 8,204,763 | B2 | 6/2012 | Elsayed et al. |
| 8,263,650 | B2 | 9/2012 | Cook et al. |
| 8,315,886 | B2 | 11/2012 | Williams et al. |
| 8,386,274 | B1 | 2/2013 | Pinsonneault |
| 8,457,988 | B1 | 6/2013 | Reardan et al. |
| 8,589,182 | B1 | 11/2013 | Reardan et al. |
| 8,589,188 | B2 | 11/2013 | Elsayed et al. |
| 8,626,531 | B2 | 1/2014 | Williams et al. |
| 8,731,963 | B1 | 5/2014 | Reardan et al. |
| 2002/0038310 | A1 | 3/2002 | Reitberg |
| 2003/0007934 | A1 | 1/2003 | Rabinowitz et al. |
| 2004/0249212 | A1 | 12/2004 | Smallridge et al. |
| 2008/0004904 | A1* | 1/2008 | Tran .................. A61B 5/0006 705/2 |
| 2009/0171697 | A1* | 7/2009 | Glauser ............. C12Q 1/6883 705/3 |
| 2010/0088778 | A1* | 4/2010 | Mulley ............... C07K 14/705 800/16 |
| 2012/0065999 | A1* | 3/2012 | Takatoku ........... G06F 19/3456 705/3 |
| 2013/0218586 | A1 | 8/2013 | Huser |
| 2014/0142140 | A1 | 5/2014 | Bird |
| 2014/0348966 | A1* | 11/2014 | Balemba ............. A61K 31/353 424/769 |

FOREIGN PATENT DOCUMENTS

| | | |
|---|---|---|
| WO | WO 01/86506 | 11/2001 |
| WO | WO 2007/073503 | 6/2007 |
| WO | 2010/104841 A2 | 9/2010 |
| WO | 2010/104841 A3 | 9/2010 |
| WO | 2014/177676 A1 | 11/2014 |

OTHER PUBLICATIONS

Ceulennans, B., Boel, M., Leyssens, K., Van Rossem, C., Neels, P., Jorens, P. G. and Lagae, L. (2012), Successful use of fenfluramine as an add-on treatment for Dravet syndrome. Epilepsia, 53: 1131-1139. doi:10.1111/j.1528-1167.2012.03495.x.*

Patani et al;, "Bioisosterism: A Rational Approach to Drug Design" Chem. Rev. (1996) 96:3147-3176.

Tran et al., "Dakin-West Synthesis of β-Aryl Ketones" J. Org. Chem. (2006) 71:6640-6643.

Cozzi et al., "Indan Analogs of Fenfluramine and Norfenfluramine Have Reduced Neurtoxic Potential" Pharmacology Biochemistry and Behavior (1998) 59(3):709-715.

Gross et al., "The influence of the sparteine/debrisoquine genetic polymorphism on the disposition of dexfenfluramine" Br J Clin Pharmacol (1996) 41:311-317.

Rothman et al., "(+)-Fenfluramine and Its Major Metabolite, (+)-Norfenfluramine, Are Potent Substrates for Norepinephrine Transporters" The Journal of Pharmacology and Experimental Therapeutics (2003) 305(3)1191-1199.

Aicardi et al., "Treatment of Self-Induced Photosensitive Epilepsy with Fenfluramine" New England Journal of Medicine (1985) 313:1419.

Aicardi et al., "Syncopal Attacks Compulsively Self-induced by Valsalva's Maneuver Associated with Typical Absence Seizures" Archives of Neurology (1988) 45:923-925.

Anonymous, "MacReportMedia—Brabant Pharma Reports Two-Year Follow-up Data From a 19-year Observational Study Using Low-Dose Fenfluramine for the Treatment of Dravet Syndrome", Nov. 25, 2013 (Nov. 25, 2013).

Arzimanoglou, Alexis, "Dravet syndrome: From electroclinical characteristics to molecular biology" Epilepsia (2009) 50(Suppl 8):3-9.

Brunklaus et al., "Prognostic, clinical and demographic features in SCN1A mutation-positive Dravet syndrome" Brain (2012) p. 1-8.

Ceulemans, "Overall management of patients with Dravet syndrome" Developmental Medicine & Child Neurology (2011) 53:19-23.

Ceulemans et al., "Successful use of fenfluramine as an add-on treatment for Dravet syndrome" Epilepsia (2012) 53(7):1131-1139.

Ceulemans B. et al., "Successful use of Fenflurarmine as add-on treatment in Dravet syndrome: a two year prospective follow up", European Journal of Paediatric Neurology (Sep. 1, 2013) vol. 17:01101866.

Chiron et. al., "The pharmacologic treatment of Dravet syndrome" Epilepsia (2011) 52(Suppl 2):72- 75.

Clemens, Bela, "Dopamine agonist treatment of self-induced pattern-sensitive epilepsy. A case report" Epilepsy Research (1988) 2:340-343.

Gentsch et al., "Laboratory Research Fenfluramine Blocks Low-Mg2'—Induced Epileptiform Activity in Rat Entorhinal cortex" Epilepsia (Jan. 1, 2000), pp. 925-928.

Meador K J., "Seizure reduction with fluoxetin in an adult woman with Dravet syndrome", Epilepsy & Behavior Case Reports, Elsevier BV, NL (Jan. 1, 2014) 2(1):54-56.

Mulley et al., "SCN1A Mutations and Epilepsy" Human Mutation (2005) 25:535-542.

Remington, "The Science and Practice of Pharmacy", Nineteenth Edition (1995), pp. 710-712.

Casaer and Boel et al., "Fenfluramine as a Potential Antiepileptic Drug" Epilepsia (2002) 43(2):205-206.

Lambert et al., "Inductive Enhancement of Aryl Participation" Journal of the American Chemical Society (Apr. 27, 1977) 99(9):3059-67.

* cited by examiner

CONTROL SYSTEM FOR CONTROL OF DISTRIBUTION OF MEDICATION

INTRODUCTION

Epilepsy is a condition of the brain marked by a susceptibility to recurrent seizures. There are numerous causes of epilepsy including, but not limited to birth trauma, perinatal infection, anoxia, infectious diseases, ingestion of toxins, tumours of the brain, inherited disorders or degenerative disease, head injury or trauma, metabolic disorders, cerebrovascular accident and alcohol withdrawal.

There are a large number of subtypes of epilepsy that have been characterized. See, for example, *Meritt's Neurology* (12th Edition). Those skilled in the art will recognize that the different subtypes of epilepsy are triggered by different stimuli, are controlled by different biological pathways and have different causes, whether genetic or environmental. The skilled addressee will also recognize that the subtypes of epilepsy vary in terms of their severity.

An example of a severe subtype of epilepsy is Dravet syndrome. Dravet syndrome is a rare and catastrophic form of intractable epilepsy that begins in infancy. Initially, the patient experiences prolonged seizures. In their second year, additional types of seizure begin to occur and this typically coincides with a developmental decline, possibly due to repeated cerebral hypoxia. This leads to poor development of language and motor skills.

Children with Dravet Syndrome are likely to experience multiple seizures per day. Epileptic seizures are far more likely to result in death in sufferers of Dravet Syndrome; approximately 10 to 15% of patients diagnosed with Dravet Syndrome die in childhood, particularly between two and four years of age. Additionally, patients are at risk of numerous associated conditions including orthopedic developmental issues, impaired growth and chronic infections.

Of particular concern, children with Dravet Syndrome are particularly susceptible to episodes of status epilepicus. This severe and intractable condition is categorized as a medical emergency requiring immediate medical intervention, typically involving hospitalization. Status epilepticus can be fatal. It can also be associated with cerebral hypoxia, possibly leading to damage to brain tissue. Frequent hospitalizations of children with Dravet Syndrome are clearly distressing, not only to the patient but also to family and carers.

In addition to Dravet syndrome, there are numerous other subtypes of epilepsy of comparable severity which are characterized by episodes of status epilepticus.

While there are national or regional differences in the systems by which patients are diagnosed and treated, generally speaking, a patient exhibiting symptoms of a condition will initially be seen by their local medical practitioner (or local hospital or clinic, in the event of severe and acute symptoms). A diagnosis will then typically be made (possibly following a referral to a specialist) and a prescription filled out by the treating practitioner. This will then be taken to a pharmacy where the prescribed medication will then be provided. For chronic conditions, repeat prescriptions will be provided by a practitioner (not always a specialist) and processed by a pharmacy in the same way.

While such systems can be adequate and function effectively for the treatment of many common conditions, there are still many potential problematic situations that can arise which result in a delay in the patient receiving their medication and/or being provided with the incorrect medication.

For example, a patient can be misdiagnosed at the outset of their therapy. Alternatively, even if correctly diagnosed, errors in transcription of that diagnosis into the patient's notes or incorrect or illegible filling out of prescriptions by the medical practitioner can occur. Additionally, shortages at the pharmacy can arise meaning that the patient either has to travel to an alternative pharmacy or return back to the pharmacy at a later date, once the pharmacy's supplies have been restocked.

For epileptic patients, especially those with severe epilepsy, any such delay or error can have disastrous results. A system is therefore needed to ensure that epileptic patients are reliably and effectively treated. To date, the inventors believe that no such systems for the treatment of epilepsy have been developed. However, examples of systems for the management of treatment of other conditions have been developed. For example, reference can be made to the Xyrem Success Program for Patients. Xyrem (sodium oxybate) is used in the treatment of narcolepsy. The drug itself has been used recreationally or as a 'date-rape' drug and thus, one aim of the Xyrem Success Program is to prevent Xyrem from being inappropriately acquired. Details of this system can be found at www.xyrem.com/patient-success-program. Various aspects of the system are also disclosed in U.S. Pat. Nos. 7,668,730, 7,765,106, 7,765,107, 779,717, 7,895,059, 8,263,650, 8,457,988, 8,589,182, and 8,731,963.

A flow chart outlining the main steps of the Thalidomid program is provided at FIG. 1. A number of issues with that program make it unsuitable for use in prescribing drugs to epileptic patients.

Firstly, the program is open to all physicians regardless of their experience in the treatment and diagnosis of the condition in question, provided that they have enrolled. While this cannot be problematic for a condition with less acutely serious symptoms, it has been found that such an approach is inappropriate for the treatment of epilepsy, especially sever subtypes of epilepsy.

Secondly, the system relies heavily on faxes between the pharmacist and physician, which is problematic, e.g. if the faxes are sent to the incorrect number, if the faxes are illegible, if there is any delay in the faxes being sent by the physician or the pharmacy, etc.

Additionally, numerous time-consuming steps have to be performed between the patient being diagnosed with the condition in question and the drug being delivered.

A further example of a system for managing the treatment of patients is the Thalidomid REMS program. Thalidomid (thalidomide) is used in the treatment of newly diagnosed multiple myeloma and moderate to severe erythema nodosum leprosum. Details of this system can be found at http://www.thalomidrems.com/. Various aspects of the system are also disclosed in U.S. Pat. Nos. 6,045,501, 6,315,720, 6,561,976, 6,561,977, 6,755,784, 6,869,399, 6,908,432, 7,141,018, 7,874,984, 7,959,566, 8,204,763, 8,315,886, 8,589,188 and 8,626,531.

A flow chart outlining the main steps of the program is provided in FIG. 2. Several aspects of that program make it unsuitable for use in prescribing drugs to epileptic patients. Firstly, the program is open to all physicians regardless of their experience in the treatment and diagnosis of the conditions in question, provided that they have enrolled. Additionally, any pharmacy can enroll to become certified and thus prescribe Thalidomid. This can be problematic as different pharmacies can store and handle data in different ways. Thus, while these systems have been found to be appropriate for the conditions in question by the regulatory authorities, it has been found by the inventor that they would not necessarily be appropriate for managing the treatment of epileptic patients, due to the specific problems associated with epilepsy and associated care.

SUMMARY

Aspects of the present disclosure include a system of controlling distribution of a medication in the treatment or prevention of epilepsy. The system can comprise a central controller having a data store and one or more processors for reading and writing data to the data store, wherein the data store comprises a database of patient records, each patient record comprising a medication authorization field, wherein the central controller outputs an authorization of a first prescription of epilepsy medication to a patient in dependence upon genetic test results for the patient and schedules one or more subsequent test for the patient prior to authorization of one or more subsequent prescription of epilepsy medication.

The systems and methods of the present disclosure can be particularly beneficial in the treatment of epilepsy, such as severe subtypes of epilepsy and/or refractory epilepsy, e.g. Dravet Syndrome, and/or for control of medicaments that have associated side effects. The central controller can authorize the first or further prescription comprising any or any combination of the following for a specified medication or active ingredient: dosage;

volume; count; regime; concentration and/or intended time period of use by the patient. The central controller can inhibit output of authorization in the event that genetic test results for the patient are absent, incomplete and/or of an incompatible data format. The central controller can instruct and/or co-ordinate the genetic test for the patient and/or the one or more subsequent test for the patient. This central management of the specific test to be carried out is particularly beneficial and can allow the central controller to dictate any or any combination of: the type of test; the test conditions/criteria; and/or the format of the test results. Additionally or alternatively, the central controller can control/authorize one or more parties to perform the test.

This centralized control of not only a prescription authorization, but also a test performed to determine suitability of a patient, is contrary to the prior art but has been determined to be particularly beneficial for controlling distribution of medication for which the side effects of the medication can have significant health implications for the patient. Such centralized controls can also reduce or prevent instances of misdiagnosis of one or more epileptic condition. This has been found to be crucial for medications which have the potential to cause physiological deterioration of one or more organs over prolonged periods of time.

In the example of the central controller prescribing the data format for the test results, the data format can be aligned with the patient test data fields and/or format of the database of patient records. This can allow a hitherto unavailable degree of automation and/or control of medication distribution to patients.

In one example, the central controller and/or data store can comprise one or more test data threshold value for authorization of a medication prescription for a patient. The central controller or data store can comprise one or more computer model or algorithm for determining whether or not to authorize a prescription of medication and/or the dosage/regime of the prescription. The central controller can log test results for one or more patient over time to generate a plot or trend in one or more test data fields. The central controller can predict future test results or one or more medication usage scenario and/or can categorize patient test data by reference to one or more predetermined models.

Such methods of control are highly beneficial in allowing determination of possible patient outcomes of treatment, for example so as to be able to adjust or cease an existing prescription in the event that it is determined to be ineffective or potentially deleterious for the patient. Additionally or alternatively, such methods can allow the control system to learn patient patterns or responses to the medication, such that the control system itself can be improved with use. Such features are beneficial in allowing ongoing development of the care program, the prescription authorization process and/or so that the central database can serve as a knowledge base.

In view of the above advantages, the systems, methods and/or central database can serve as a research tool for improving understanding of one or more drug and/or managing an associated care program. Furthermore the amassing of information of the kind described herein within a central, access-restricted database allows relevant data to be exported to necessary authorities, including regulatory authorities such as the Food and Drug Administration, European Medicines Agency, the Medicines and Healthcare products Regulatory Agency, or similar organizations.

The controller can allow for reporting of statistics, trends or outcomes of the care program, for example to regulatory bodies and/or research partners or other organizations. The central maintenance of such records, e.g. in a prescribed format, can thus be an important feature in the implementation of the invention.

According to various examples of the present disclosure, the subsequent test can differ from the genetic test. The subsequent test can comprise a physiological test and/or genetic test.

The central controller can schedule (e.g. automatically) one or more subsequent test for the patient, for example at the time of receipt of patient test results or upon outputting a prescription authorization or upon confirmation of delivery/receipt of an authorized prescription to/by the patient. The central controller can schedule a specific time/date and or a time period over which the subsequent test is to be performed. The timing of the subsequent test is typically within the time period in which an authorized prescription would be used.

The central controller can output an initial or subsequent time period over which use of the medication by the patient is authorized, e.g. beyond which subsequent test results for the patient are required to be received before a following period of use for the patient can be authorized. In one example, the timing of a repeat prescription request, e.g. from a patient or physician, will be checked against the time period determined by the central controller and can beneficially allow monitoring of patient compliance.

The central controller can authorize a repeat prescription of the medication dependent upon subsequent test results. The central controller can alter the prescription and/or the authorized time period until a subsequent test is required based on the patient test results.

In one example, a patient record can only be created on the database if genetic test results are available for the patient. Entering a patient onto the database can be inhibited by the central controller unless a predetermined format or a minimum selection of test data fields for the patient are received by the central controller. This ability to vet patients before there is any possibility of authorizing a prescription is beneficial as a fail-safe to ensure that an individual patient cannot be incorrectly issued an unauthorized prescription, e.g. by human error. When combined with the ability of the central controller to control the initial and/or subsequent patient tests, this provides a particularly stringent system for managing patient diagnoses and drug distribution.

The control centre can issue a prescription authorization and/or distribute the associated medication, either itself or via an affiliated distributor. A confirmation of receipt of the medication by the patient can be provided to the control centre, for example including a time/date of receipt. The confirmation can comprise data indicating any or any combination of the following for a specified medication or active ingredient of the delivered prescription: dosage; volume; count; regime; concentration and/or time period of use by the patient. Thus, delivered medication can be verified by the central controller.

The central controller can initiate delivery of prescriptions to patients. The database can comprise one or more delivery address field for each patient. The delivery can be made direct to a patient and/or cannot involve the prescribing physician. Thus, the central controller can act as a centralized pharmacy. Additionally or alternatively, the central controller can provide a central prescription authorization controller, which instructs associated pharmacies whether or not to provide prescriptions to end patients. Each associated pharmacy can require approval by the central controller prior to allowing distribution of prescriptions in accordance with the invention.

The subsequent medical test of a patient can or cannot comprise test for a change in clinical status of the patient. The subsequent medical test can comprise an assessment of the structure and/or function of one or more specific organ. The subsequent test can comprise imaging of the one or more specific organ, such as by way of sonography, echocardiography or other convenient technique. The one or more specific organ can or cannot comprise the heart. The test results can or cannot comprise one or more images of the organ, such as an echocardiogram. The test results comprising the one or more image can be transmitted to the central controller. Additionally or alternatively, summary data or processed/derived accompanying data can be transmitted.

The system can comprise one or more portable or wearable electronic device for monitoring patient health. The electronic device can comprise one or more sensors for measuring one or more indicators of patient wellbeing, such as, for example, any or any combination of blood pressure, echocardiography, electrocardiography (ECG), heart rate, blood oxygen, temperature, lung function. The electronic device can take readings indicative of the function of one or more organ, which can be the organ that is the focus of the subsequent test.

The electronic device can be arranged to transmit sensor data, or a subset or processed set or results of the sensor data, to—or for receipt by—the central controller. The sensor results can be processed, e.g. by the electronic device or central controller, such that only specific sensor data entries or results are recorded by the controller on the central data store (e.g. on the patient database). Thus continuous, ongoing or intermittent patient monitoring can be used and the sensor data processed such that only key indicators can be logged on the central data store. For example, one or more algorithms can be used to process the sensor data and to output an indication of normal or abnormal, or a deterioration in, patient wellbeing in response to the care program.

The results from the electronic device can be used by the central controller to determine/output a change to a scheduled medical test for the patient and/or a change to authorization of a prescription or a change to a medication prescription.

The central data store can comprise a database of authorized carers, such a medical professionals. The authorization of a patient for treatment and/or prescription can require the patient entry to be linked to a physician contained within the database of authorized carers. This can allow control of physicians who are able to prescribe the medication. This unprecedented level of control can be used to ensure that only leading experts or pre-vetted professionals are authorized to prescribe the drug. In a second aspect of the present disclosure there is provided a method of controlling distribution of medication, such as one or more drug, corresponding to the system of the first aspect. The method or system can comprise a method/system for operating a patient care program. In a third aspect of the present disclosure, there is provided a data carrier comprising machine readable instructions for the control of one or more processor to function as a central controller in accordance with the first or second aspect.

Wherever practicable, any of the essential or preferable features defined in relation to any one aspect of the present disclosure can be applied to any further aspect. Accordingly, embodiments of the invention can comprise various alternative configurations of the features defined above.

BRIEF DESCRIPTION OF THE DRAWINGS

Embodiments of the invention are described in further detail below by way of example only with reference to the accompanying drawings, of which.

DETAILED DESCRIPTION

Figure 1:
FIG. 1 shows a flow diagram of steps involved in a first example of a care program according to the prior art.
Figure 2:
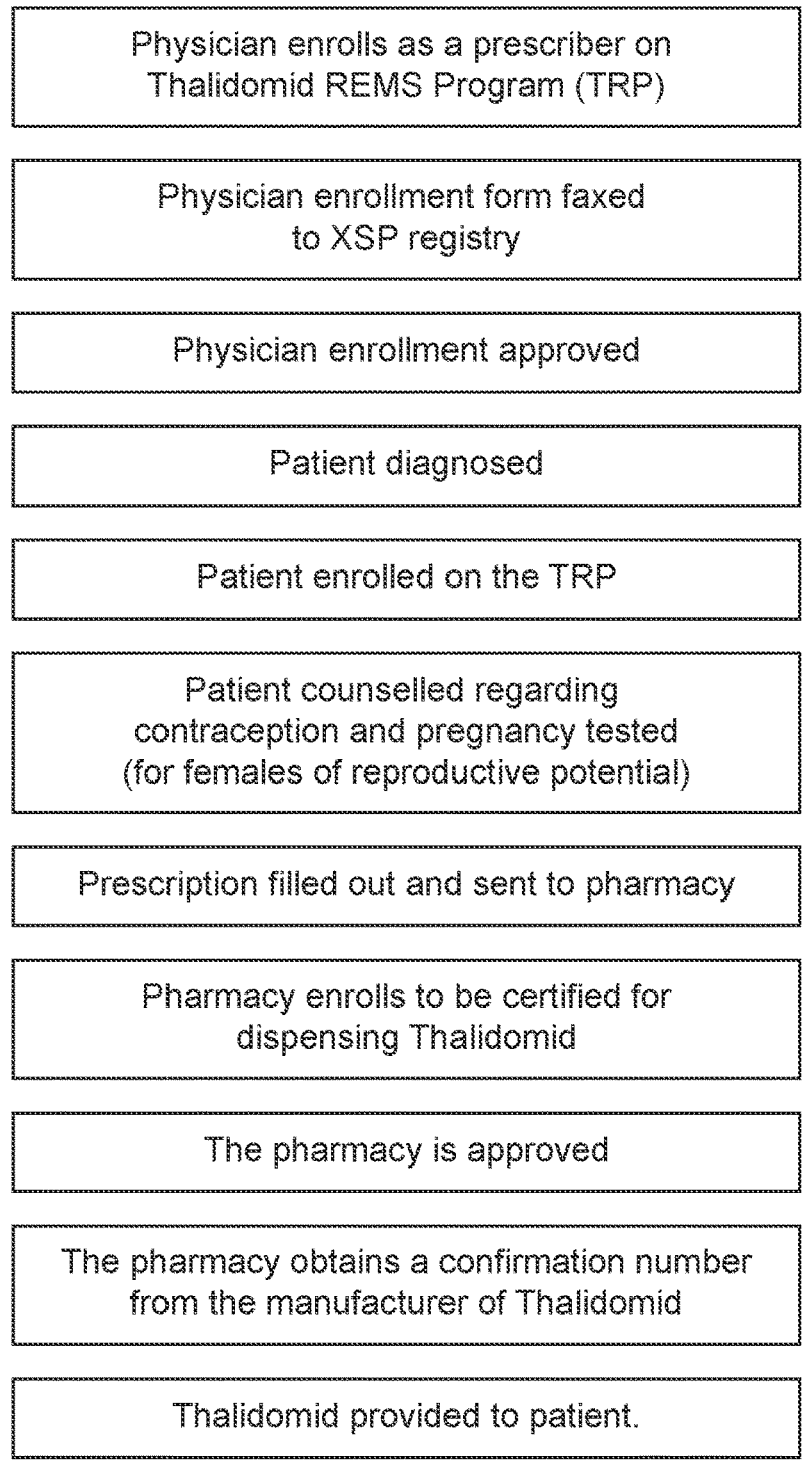
FIG. 2 shows a flow diagram of steps involved in a second example of a care program according to the prior art.

As summarized above, a system and method for centralized control of a care program and issuance of associated prescriptions is provided. Prior art care programs typically focus on care program risk management. In contrast, the embodiments of the present disclosure described herein aim to facilitate a more comprehensive patient care program, which can encompass each of: i) confirmation of diagnosis, ii) verifying compliance, iii) monitoring side effect profile and/or identifying failures in efficacy. Systems according to the prior art are unsuitable for treatment of epilepsy, and, in particular, certain sever forms of epilepsy. The system described and claimed herein is also appropriate for use with managing the treatment of patients who suffer from other conditions, the care of which involves the same or similar concerns with respect to symptom severity, diagnoses, compliance, side effects and efficacy. The present disclosure provides a care program involving one or more drugs known to negatively impact the life expectancy of a patient. The subject systems and methods are suitable for care programs for which the prescribed drug(s) have a cumulative deleterious effect on patient health over prolonged periods of time, such as months or years. In such circumstances, the careful prescribing and distribution of the drug can be used to control the balance struck between drug efficacy and the negative impact on other aspects of patient health.

The subject systems and methods were developed for use with certain of such drugs as are described below which have side effects that require greater control than provided for by the prior art. In such instances, it has been found that the control of an initial prescription and/or ongoing repeat prescriptions according to specific patient tests can significantly improve patient outcome.

There are a vast number of subtypes of epilepsy. While all forms of epilepsy are distressing both to the patients themselves as well as their parents, carers and friends, some subtypes of epilepsy are more severe than others. By 'severe' reference is made to, for example, subtypes of epilepsy that are intractable and/or which are characterized by episodes of status epilepticus. Such subtypes of epilepsy include, but are not limited to, Dravet syndrome, Lennox-Gastaut syndrome, West syndrome, Doose syndrome and/or other types of refractory epilepsy.

The system described and claimed herein is appropriate for use with managing the treatment of epileptic patients using any convenient drug, whether provided alone, as a formulation or as a composition containing other bioactive drugs, that is useful in treating epilepsy. In some aspects, the drug is a receptor agonist, antagonist or allosteric modulator. In certain aspects, the drug is active at one or more 5-HT receptor sub-types and/or sub-units thereof. In some aspects, the drug affects neurotransmitter or neuropeptide synthesis, storage, release, degradation, reuptake and/or activity. In another aspect, the drug is an ion channel blocker. In certain aspects, the drug is one which alters the balance between excitatory and inhibitory neurotransmissions in the brain of an epileptic patient. In some aspects, the drug is one known to be effective in epileptic patients having one or more genetic mutations. In certain aspects, the drug is one shown to be effective in epileptic patients who are unresponsive to drugs commonly used to treat epilepsy.

In some aspects, the system is appropriate for use with managing the treatment of epileptic patients using a drug, a drug formulation, or a drug composition which affects either directly or indirectly, the activity of one or more 5-HT receptors in the brain of a patient when an effective dose of those compounds or compositions are administered to said patient. In some embodiments, the one or more 5-HT receptors are selected from one or more of $5\text{-HT}_1$, $5\text{-HT}_{1A}$, $5\text{-HT}_{1B}$, $5\text{-HT}_{1C}$, $5\text{-HT}_{1D}$, $5\text{-HT}_{1E}$, $5\text{-HT}_{1F}$, $5\text{-HT}_2$, $5\text{-HT}_{2A}$, $5\text{-HT}_{2B}$, $5\text{-HT}_{2C}$, $5\text{-HT}_3$, $5\text{-HT}_4$, $5\text{-HT}_5$, $5\text{-HT}_{5A}$, $5\text{-HT}_{5B}$, $5\text{-HT}_6$, and $5\text{-HT}_7$, amongst others. In certain embodiments, the drug is a receptor agonist, antagonist, or allosteric modulator.

Thus, according to one aspect of the present invention, there is provided a system appropriate for use with managing the treatment of an epileptic patient using a drug, drug formulation or drug composition that affects the activity of one, some or all of the afore-mentioned receptors In some aspects, the system disclosed and claimed herein is appropriate for use in managing the treatment of epileptic patients using a drug, drug formulation or drug composition which is efficacious in affecting the synthesis, storage, release, degradation, reuptake, and/or activity of one or more neurotransmitters or neuropeptides involved in triggering one or more symptoms of epilepsy or affecting their severity, frequency or duration. In certain embodiments of this aspect of the invention, the neurotransmitter can be one or more of dopamine, serotonin, gamma aminobutyric acid (GABA), among others. In one exemplary embodiment, the neurotransmitter is serotonin.

In another aspect of the invention, the system is appropriate for use with managing treatments that employ drugs which acts as ion channel blockers. In one embodiment the drug is a sodium channel blocker.

In some aspects, the system disclosed and claimed herein is appropriate for use with managing the treatment of epileptic patients using drugs, drug formations or drug compositions which are efficacious in preventing or treating symptoms of epilepsy in patients having one or more genetic mutations. Such mutations can include but are not limited to mutations implicated in the onset, frequency, severity or duration of epilepsy symptoms, including but not limited to seizures. Examples of such mutations include but are not limited to: mutations in the SCN1A (such as partial or total deletion mutations, truncating mutations and/or missense mutations e.g. in the voltage or pore regions S4 to S6), SCN1 B (such as the region encoding the sodium channel .beta.1 subunit), SCN2A, SCN3A, SCN9A, GABRG2 (such as the region encoding the .gamma.2 subunit), GABRD (such as the region encoding the .delta subunit) and/or PCDH19 genes. Thus, according to a further aspect of the present invention, there is provided a system appropriate for use with managing the treatment of an epileptic patient that exhibits a mutation in one, some or all of the above genes.

In some aspects, the system disclosed and claimed is appropriate for use with managing the treatment of patients who are young. In certain embodiments, the patients is under 18 years of age, such as under 15, under 10, under 5, under 2, under 18 months, under 1 year of age, under 6 months, or from 1 month to 6 months of age. In certain embodiments, the patients is 18 years of age or less, such as 15 years of age or less, 10 years of age or less, 5 years of age or less, 2 years of age or less, 18 months of age or less, 1 year of age or less, 6 months of age or less, or from 1 month to 6 months of age.

In certain aspects, dosing frequency and amounts will vary according to individual patient needs. Dosing can be twice daily, daily, every other day, four times weekly, three times weekly, five times weekly, six times weekly, once a week, bi-weekly or once a month. Dosing amounts will vary according to patient parameters which include but are not limited to, age, weight, and severity, frequency and/or nature of symptoms. In certain embodiments, dosing is in an amount of less than about 0.8 mg/kg/day, about 0.7 mg/kg/day, about 0.6 mg/kg/day, about 0.5 mg/kg/day, about 0.45 mg/kg/day, about 0.4 mg/kg/day, about 0.35 mg/kg/day, about 0.3 mg/kg/day, about 0.25 mg/kg/day or about 0.2 mg/kg/day to about 0.1 mg/kg/day, about 0.05 mg/kg/day, or about 0.01 mg/kg/day is employed. In certain embodiments, dosing of a drug of interest is performed in an amount of 0.8 mg/kg/day or less, such as 0.7 mg/kg/day or less, 0.6 mg/kg/day or less, 0.5 mg/kg/day or less, 0.45 mg/kg/day or less, 0.4 mg/kg/day or less, 0.35 mg/kg/day or less, 0.3 mg/kg/day or less, 0.25 mg/kg/day or less, 0.2 mg/kg/day or less, 0.1 mg/kg/day or less, 0.05 mg/kg/day or less, or 0.01 mg/kg/day or less.

In a further aspect, the dosage is administered orally, by intramuscular or intravenous injection or by any other convenient means.

Drugs used in treatments with which the systems of the present disclosure are useful can be administered alone, or as a drug formulation in which the drug is combined with inactive ingredients, which can include dispersants, preservatives, buffers, dyes or flavoring agents, among others. The drugs can also be administered along with other agents that can also be active against epilepsy or have other biological activity.

Any convenient drugs can find use in the subject systems and methods. In certain embodiments, the system is useful for managing treatments employing one or more of the following drugs: cannabidiol, carbamazepine, clemizole, clobazam, fenfluramine, midazolam, stiripentol, topiramate and valproate. In certain embodiments, the drugs can be chemical derivatives, or metabolites of those compounds. In certain embodiments, the drug is conjugated to an antibody or antibody-derived peptide which, in some cases, can affect drug specificity, activity, half-life, metabolism or other facets of bioactivity.

In some instances, the drug is a cannabinoid. In some cases, the cannabinoid is a cannabimimetic, such as, 9-tetrahydrocannabinol. Cannabinoids of interest include, but are not limited to, 4,5-dihydro-2-methyl-4(4-morpholinylmethyl)-1-(1-naphthalenyl-carbonyl)-6H-pyrrolo[3,2,1-i,j]quinolin-6-one [R(+)WIN55,212] cannabidiol, a derivative thereof, a metabolite thereof or a conjugate thereof. In some instances, the drug is carbamazepine, a derivative thereof, a metabolite thereof or a conjugate thereof. In some instances, the drug is clemizole, a derivative thereof, a metabolite thereof or a conjugate thereof. In some instances, the drug is clobazam, a derivative thereof, a metabolite thereof or a conjugate thereof. In some instances, the drug is midazolam, a derivative thereof, a metabolite thereof or a conjugate thereof. In some instances, the drug is stiripentol, a derivative thereof, a metabolite thereof or a conjugate thereof. In some instances, the drug is topiramate, a derivative thereof, a metabolite thereof or a conjugate thereof. In some instances, the drug is valproate, a derivative thereof, a metabolite thereof or a conjugate thereof.

In some instances, the drug is a fenfluramine active agent, such as fenfluramine, a derivative thereof, a metabolite thereof or a conjugate thereof. In certain aspects, the drug is a chemical derivative of fenfluramine. In certain instances, the drug is a fenfluramine antibody conjugate. In some embodiments, the fenfluramine active agent is fenfluramine, or a pharmaceutically acceptable salt thereof. In certain embodiments, the fenfluramine active agent is an analog of fenfluramine, or a pharmaceutically acceptable salt thereof. Fenfluramine analogs of interest include, but are not limited to, those analog compounds that are resistant to N-dealkylation, e.g., via action of metabolizing enzymes such as CYP2D6. In some cases, the fenfluramine analogs have structures that impart reduced CYP2D6 affinity on the molecule, while retaining a desirable target activity. In certain instances, the fenfluramine analogs have structures that impart resistant to metabolism by CYP2D6. Fenfluramine compositions and formulation that find use in the subject systems and methods include those described in WO2014/177676.

Any convenient methods of treating epilepsy may be performed in conjunction with one or more aspects of the subject methods and systems (e.g., as described herein), including but not limited to, those methods described in WO2014/177676, the disclosure of which is herein incorporated by reference in its entirety.

Aspects of the subject methods include treating and/or preventing epilepsy in a patient comprising administering an effective dose of a fenfluramine active agent (e.g., fenfluramine) or a pharmaceutically acceptable salt thereof to the patient. In certain embodiments, the method includes preventing and/or ameliorating seizures in a patient diagnosed with epilepsy comprising administering an effective dose of a fenfluramine active agent (e.g., fenfluramine) or a pharmaceutically acceptable salt thereof to the patient. In certain instances, the fenfluramine active agent is fenfluramine. In certain instances, the fenfluramine active agent is a fenfluramine derivative. In certain instances, the fenfluramine active agent is a fenfluramine metabolite. In certain instances, the fenfluramine active agent is a fenfluramine conjugate. In certain instances, the patient is suffering from Dravet syndrome.

Aspects of the subject methods include treating and/or preventing Dravet Syndrome in a patient comprising administering an effective dose of fenfluramine active agent (e.g., fenfluramine) or a pharmaceutically acceptable salt thereof to the patient. In certain embodiments, the method includes preventing and/or ameliorating seizures in a patient diagnosed with Dravet Syndrome comprising administering an effective dose of a fenfluramine active agent (e.g., fenfluramine) or a pharmaceutically acceptable salt thereof to said patient. In certain instances, the fenfluramine active agent is fenfluramine. In certain instances, the fenfluramine active agent is a fenfluramine derivative. In certain instances, the fenfluramine active agent is a fenfluramine metabolite. In certain instances, the fenfluramine active agent is a fenfluramine conjugate. In some embodiments of the method, the patient exhibits a mutation in one, some or all of the genes selected from the group consisting of SCN1 A, SCN1 B, SCN2A, SCN3A, SCN9A, GABRG2, GABRD and PCDH19, and the method includes administering to the patient an effective dose of fenfluramine active agent (e.g., fenfluramine) or a pharmaceutically acceptable salt thereof.

Aspects of the present disclosure include a method of stimulating one or more 5-HT receptors in the brain of a patient by administering an effective dose of fenfluramine active agent (e.g., fenfluramine), or a pharmaceutically acceptable salt thereof, to the patient, the one or more 5-HT receptors being selected from the group consisting of one or more of 5-HT1, 5-HT1A, 5-HT1s, 5-HT1c, 5-HT1D, 5-HT1E, 5-HT1F, 5-HT2, 5-HT2A, 5-HT2s, 5- HT2c, 5-HT 3, 5-HT4, 5-HTs, 5-HTsA, 5-HTss 5-HT 6, and 5-HT7. In certain embodiments of the method, the patient has been diagnosed with Dravet Syndrome.

In certain embodiments of the methods described herein, the effective dose is less than about 0.5 mg/kg/day to about 0.01 mg/kg/day. In certain embodiments, the effective dose is administered in the form of one or more dosage forms for oral, injectable, transdermal, inhaled, nasal, rectal, vaginal or parenteral delivery. In certain embodiments, the one or more dosage forms are liquid formulations. In certain instances of the method, the fenfluramine active agent is employed as a monotherapy. In certain cases, the effective dose of fenfluramine active agent (e.g., fenfluramine) or a pharmaceutically acceptable salt thereof, is coadministered with one or more co-therapeutic agents. In certain embodiments, the one or more co- therapeutic agents is selected from the group consisting of carbamazepine, ethosuximide, fosphenytoin, lamotrigine, levetiracetam, phenobarnitol, progabide, topiramate, stiripentol, valproic acid, valproate, verapamil, and benzodiazepines (such as clobazam, clonazepam, diazepam, ethyl loflazepate, lorazepam and midazolam) or a pharmaceutically acceptable salt thereof. In certain embodiments, the patient is aged 18 or less.

In certain embodiments, the centralized control is provided by an organization, in some cases, a drug development and/or supply organization. The control measures are in some cases provided by machine-readable code in the form of software or firmware running on a computer system network under the control of the organization. However certain control measures can be implemented at least in part by manual intervention in conjunction with the control software and, accordingly, various combinations of manually initiated and/or automatically initiated control steps are envisaged as will be understood by the person skilled in the art.

Figure 3:
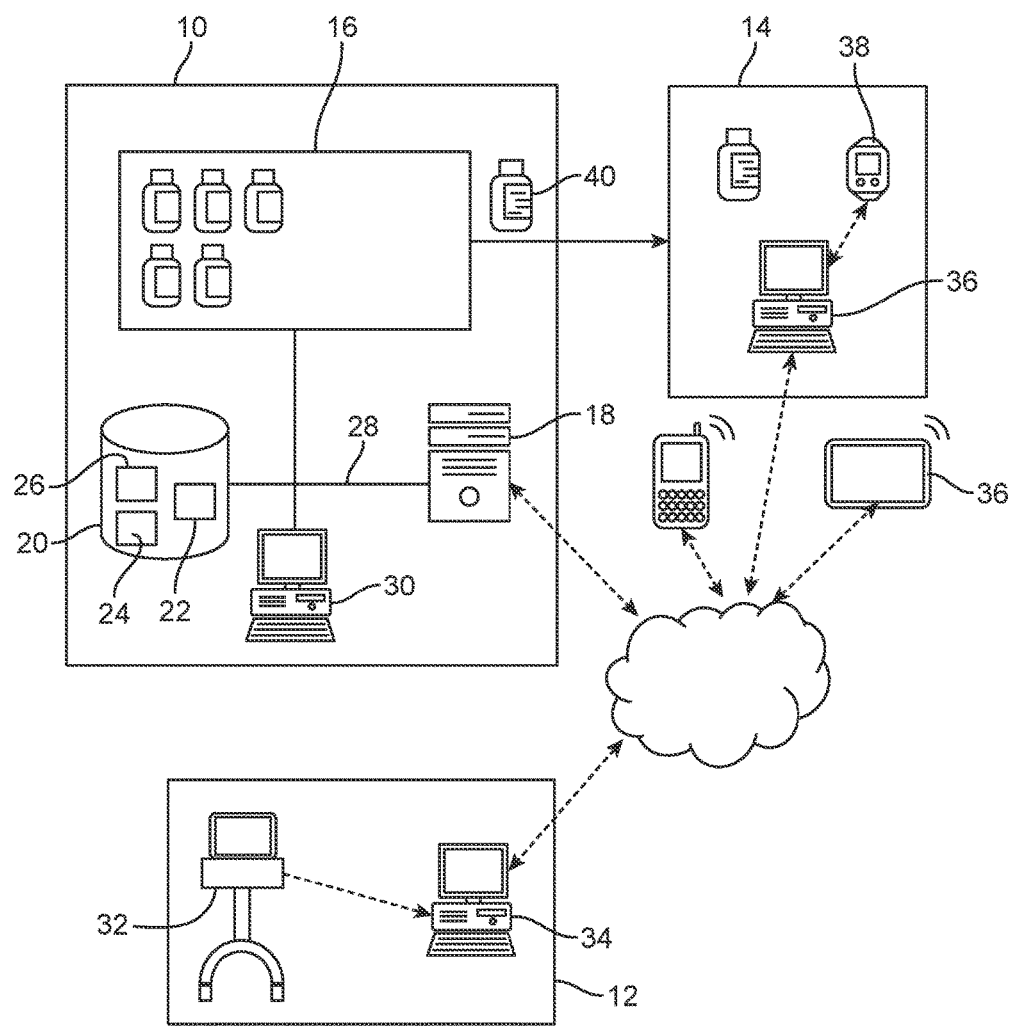
FIG. 3 shows an embodiment of a system and network according to the present disclosure.

Turning firstly to FIG. 3, there is provided an overview of a system according to an example of the invention, comprising a central control system 10, a medical facility 12 responsible for care of a patient and a patient residence 14. The examples of the invention described below rely on data communications between suitable devices and, as such, it is possible in certain examples of the invention, that the required data communications are made via electronic devices, e.g. portable communication devices, associated with the patient and/or care provider rather than premises or residences. As such, although a common implementation of the invention would comprise the different premises 12 and 14, they are not essential to the definition of the invention.

The central control system 10 comprises a drug storage facility 16, typically a secure storage facility with restricted access, and can allow the central control facility to act as a central pharmacy for one type, or limited number, of drugs prescribed in accordance with the invention. The computer system for operation of the central control system can be co-located with the facility 16 or else can be remotely located but in communication therewith, for example over a local or wide area network as necessary.

The computer system underpinning the central control system 10 comprises one or more server 18 for controlling transmission and receipt of data communications to/from the central computer system, in some cases via the internet, e.g., via TCI/IP communications, or other suitable wide area network over which the central control system 10 can communicate with patients and/or the relevant medical professionals.

The central computer system further comprises a data store 20, comprising one or more non-volatile data storage devices, on which is maintained a patient database 22. In this example, the data store 20 further comprises a medical professional, e.g. a physician, database 24 and/or a drug inventory database 26 for the drug storage facility 16. The overall data store 20 can be located at a single location or distributed over a plurality of locations as required, for example with different databases or portions thereof maintained at different locations/premises.

The server 18 and data store 20 can be provided as part of a local area network 28. The central controlling network 28 can comprise one or more further electronic devices 30, such as PC's in order to allow operator interaction with the central control system. Such electronic devices allow via one or more suitable interface, any or any combination of data input, data editing, data viewing/searching and/or data output, for example by instructing transmission of data from the data store to a recipient, printer or other conventional output device. The one or more operator electronic device in some cases comprises a screen or other conventional display equipment. A plurality of servers 18 and/or operator devices 30 can be accommodated for access to a common data store 20.

The medical facility 12 in some cases comprises a hospital, surgery center, clinic or similar, with which one or more physician is associated for treatment of epilepsy. Suitable physicians can include acknowledged experts, and in some cases leading experts, in the relevant medical condition or field of treatment.

Equipment 32 for performing one or more medical test in accordance with the present disclosure can be provided at the medical facility 12, or deliverable thereto under the control of the central computer system. A communication device 34 associated with the medical facility and/or expert physician allows remote data communication with server 18 for the purpose of the invention.

The system further comprises one or more patient electronic communication device 36, such as a PC, laptop, cellphone, tablet computer or similar device by which the patient can transmit/receive communications with the server 18 or communication device 34. The patient device is particularly used to communicate drug delivery communications between the patient and central control system. In certain instances, functions assigned to the patient device 36 concerning the delivery and/or receipt of a prescription can be assigned to the medical facility device 34 or a local pharmacy for confirming delivery/receipt of a prescription by the patient.

In some instances, the system also comprises a patient monitoring device 38 comprising one or more sensors for measuring one or more physiological parameters indicative of patient wellbeing. In certain instances, the monitor comprises one or more sensor for measuring heart function, such as a heart rate and/or blood pressure sensor. The patient monitoring device in some cases comprises a portable and/or wearable electronic device, for example, having a power source, capable of outputting readings to the patent communication device 36 and/or directly to server 18 or medical facility device 34. For example, a wrist strap device or else a device integrated with, or in communication with, a cell phone or similar can be used for this purpose, in a manner similar to conventional health monitoring technology. However, the patient monitoring device 38 is, in some cases, configured for automated communication with the server 18 either directly or indirectly in order to ensure data of the required format and or at required timings/intervals is provided.

The patient monitoring device 38 can also be pre-programmed for taking and/or compiling measurements in a predetermined format, for example, over a predetermined duration or according to a predetermined number of variables or readings. In certain cases, the patient monitoring device can only transmit sensed data when said predetermined parameters have been met, for example to ensure consistency of readings and/or to ensure a predetermined data format is recognizable to server 18. Additionally or alternatively, the data transmitted by the patient monitoring device can comprise one or more identifier, by way of packet header data, metadata, IP address or similar, so as to indicate the patient record to which the data relates. This can allow automatic updating of the patient database 22 at the central control system upon receipt of the relevant readings or associated/derived data from the patient monitoring device.

Figure 5:
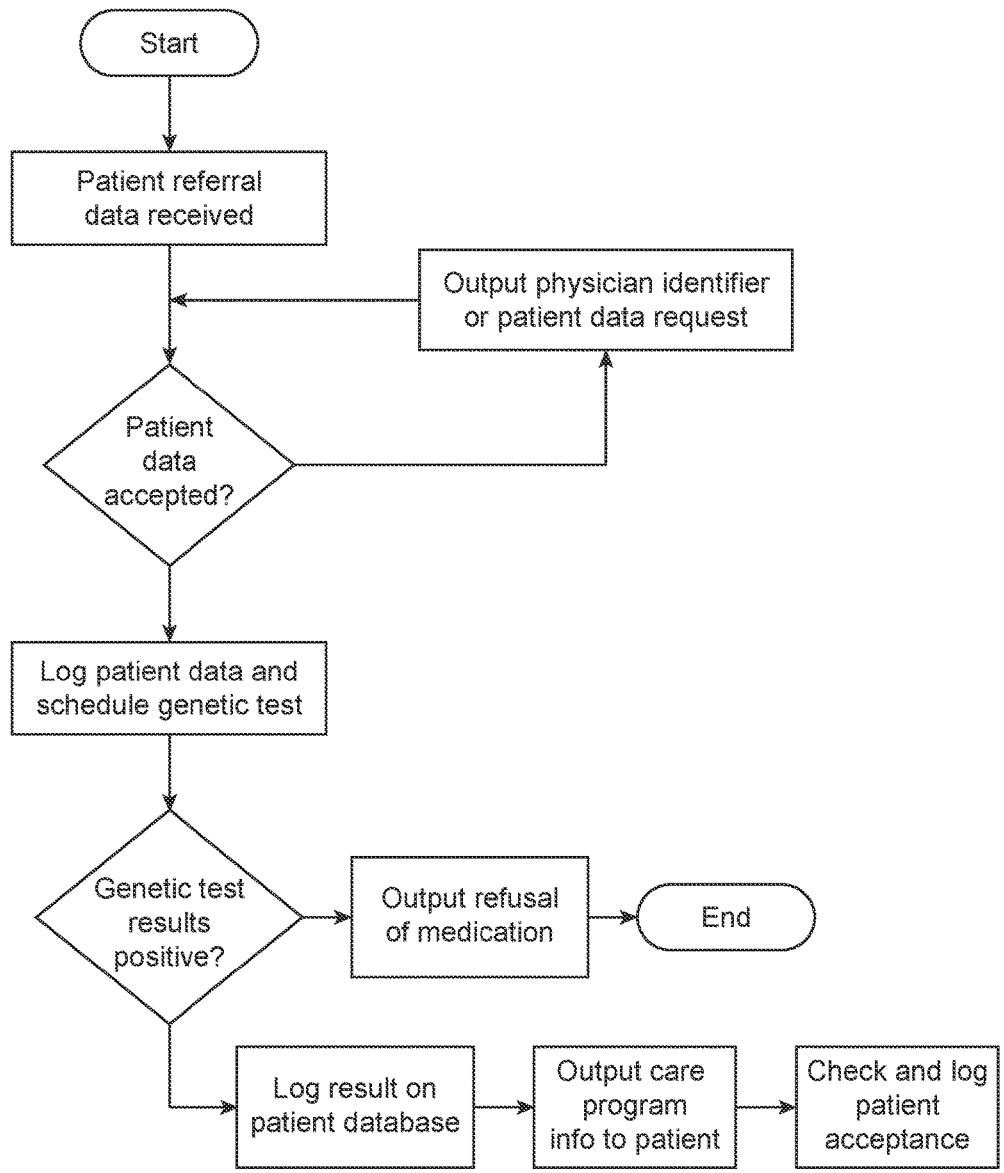
FIG. 5 shows a flow diagram of steps involved in a patient approval process according to an embodiment of the present disclosure.
Figure 6:
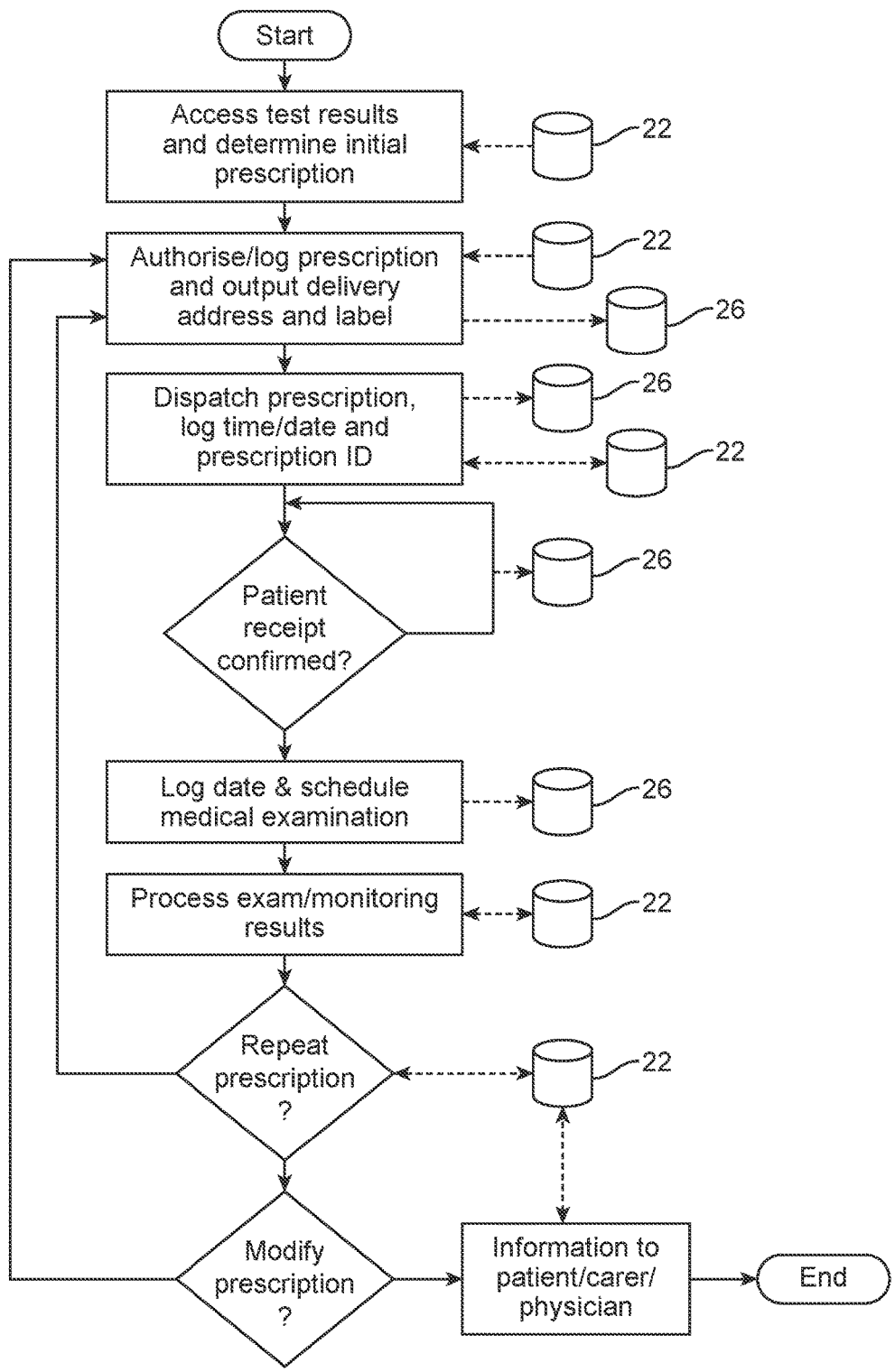
FIG. 6 shows a flow diagram of a drug distribution process according to an embodiment of the present disclosure.

An example of a method of operation of an epilepsy care program using the above-described system is described below with reference to FIGS. 4-6.

Figure 4:
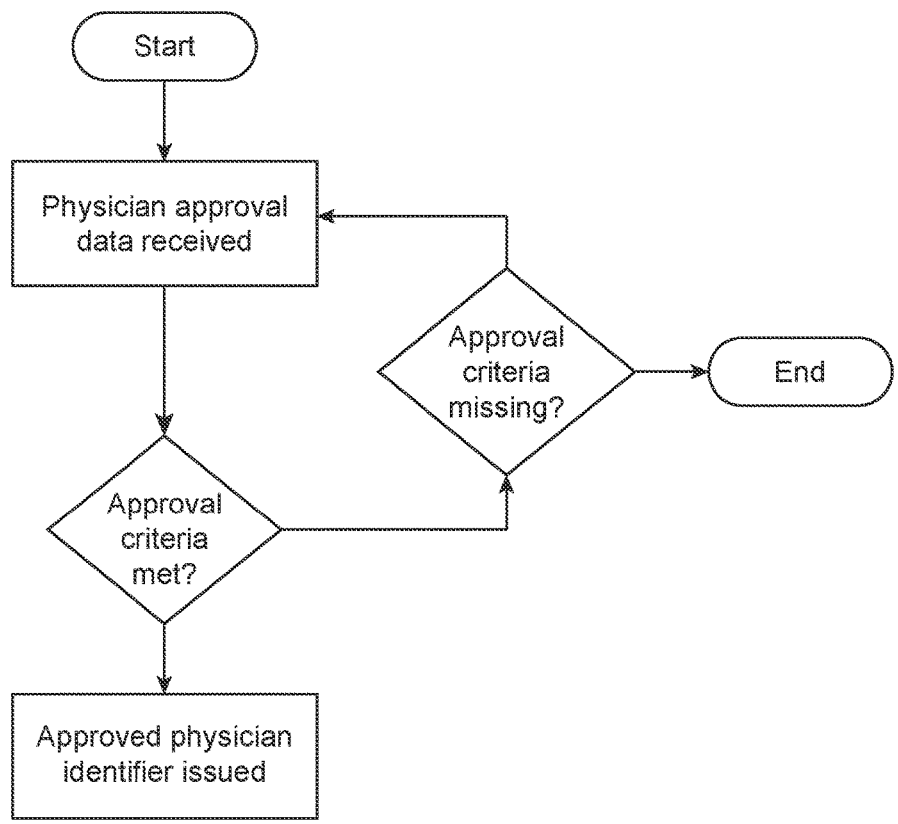
FIG. 4 shows a flow diagram of steps involved in a physician approval process according to an embodiment of the present disclosure.

A primary requirement of the operation of the care program system is that a physician proposing the prescription of drugs to a patient must first be identifiable and pre-approved on the central computer system, as shown in FIG. 4, before a request to either enter a patient onto the patient database, or else prescribe a drug to a patient can be authorized. Approval of a physician for referral of patients to the care program requires a number of checks for the physician to be satisfied.

Such checks can include one or more of the following criteria in the relevant field of patient care: the physician's qualifications; years of practice; reputation as an expert; number of published articles and/or verified referees. In certain embodiments, it is intended that the approval criteria will ensure a high threshold such that approval will only be available to leading experts in the field, rather than being open to any qualified physician or specialist.

In certain embodiments, the prescriber of drugs under the care program can additionally or alternatively require approval before a prescription can be authorized by the central control system. Any or any combination of the above approval criteria can be applied to a process for approving a prescriber of drugs under the care program. A prescriber can be approved upon receipt of references from one or a predetermined number of approved physicians/referrers.

The physician database 24 contains details of approved physicians and the associated approval criteria, for example by way of a plurality of fields relating to the approval criteria logged for each physician. An approved status field can also be provided for each physician entry in the database 24. The database 24 can comprise details of physicians pending approval, whereby certain approval fields are incomplete or insufficient to allow approval to be authorized.

The physician database in some cases comprises a unique identifier for each physician as well as the physician's name, contact details and associated medical establishment or employer. An approval ranking can be established and provided in a further field for each physician in the database 24.

Once approved, a physician can refer a patient to the care program by transmitting an associated request to the server 18 comprising certain mandatory data fields, including the patient name, postal address details and any other suitable contact details. The request can include a diagnosis or severity indicator or associated test results for a patient. The patient referral request is processed upon receipt by the server 18 as shown in FIG. 5. Patient details are logged on the patient database 22 upon receipt by server. Each patient record comprises a field indicating the referring physician using an identifier corresponding to the associated entry in the physician database 24. Only once registered with a corresponding identifier for a pre-approved physician can a patient be assessed for authorization of medication under the program.

The patient suitability assessment process comprises analysis of the results of a medical patient examination, in some cases comprising a genetic test. The genetic test is scheduled and performed under the control of the central control system 10, i.e. by the drug company controlling distribution of the drug in question. Control of the patient suitability screening process in this manner ensures that tests can be performed to specific standards of compliance and/or that test results data can be provided in a predetermined format that can be vetted by software running on the Upon patient approval, a proposed genetic test schedule is output by the central control system and transmitted to the patient, physician and/or a test operator. The test operator can comprise one or more employee of the drug company and/or an organization vetted and approved by the drug company to perform the test according to predetermined conditions. Once agreed by the recipients the genetic test is scheduled and the time/date logged, whereby the central control system awaits receipt of the test data.

If the genetic test results do not pass the patient approval criteria, a communication is sent to the corresponding physician and/or patient indicating unsuitability for the care program. In certain instances, a log of successful/unsuccessful patient referral requests can be maintained for each physician. In certain instances, the genetic test is critical as only patients with specific genetic mutations have the indication in question. Given the adverse side effects of the drug, in some cases, those patients should not be treated unless absolutely necessary.

In addition to the genetic test, one or more physiological examination can be performed under the control of the care program operator to determine a patient's susceptibility to one or more known side effects of the care program medication. Such examination can comprise imaging of, and/or testing the function of one or more patient organ. In a care program for one or more sever epilepsy sub-type, certain medication can cause degradation of the heart and accordingly an echocardiogram or other cardiovascular examination can be performed in such cases.

If the genetic and/or physiological test results meet the approval criteria, the test results can be logged and the patient record updated to an approved status for the care program. Information on the care program, including the potential side effects of the drug, is provided to the patient by way of suitable media, comprising a web site, data carrier, documents or other conventional means. In certain cases, the patient or guardian is required to confirm that he/she has reviewed, understood and accepts the risks associated with the care program medication. Patient acceptance can be logged by the central computer system on the patient record in database 22 prior to entering the prescription distribution and patient monitoring phase of the program as depicted by FIG. 6.

In certain instances, an initial drug prescription for the patient is determined by the central control system 10 in accordance with patient data logged in the database, such as age, gender, height/weight, medical history and/or test results. The central computer system, such as for example PC 30 or server 18 outputs a prescription label comprising patient and prescription data to be applied to one or more container 40 for the prescription. In some cases, the system also outputs a delivery document or label containing a delivery address for the prescription. Any such documents/labels can be printed at the storage facility for application to the prescription prior to shipment.

In certain instances, the initial patient prescription is packaged, labelled and dispatched from the drug storage facility 16 according to the details output by the central control system. The time and date of prescription dispatch can be logged on the patient record and a confirmation of receipt field is provided in the patient database 22. Positive confirmation of receipt of the prescription by the patient or medical facility 12 can be provided to the server 18 and logged in the patient database 22. Such confirmation can be provided by completing a prescription receipt form online, in some cases requiring the recipient to log into an online web site or portal administered by the server 18. Additionally or alternatively, each prescription can comprise a unique identifier, such that confirmation of receipt is only verified by return communication of the unique identifier to the server 18 by the recipient. Thus positive acknowledgement of the recipient and prescription can be accommodated. In certain instances, a portable communication device carried by the courier can provide an interface for positive verification of prescription receipt in the manner described above.

The time/date of receipt of the prescription can be logged on the patient record along with an associated prescription time period or length. The system can then output a deadline by which a repeat prescription is to be authorized, prior to, or else coinciding with, the cessation date of the initial prescription. Unlike conventional repeat prescriptions, a repeat or further prescription under the care program is not authorized by the central control system unless satisfactory further medical assessment results for the patient are logged on the patient database 22. Such results can be obtained by ongoing patient monitoring using a patient monitoring device issued to the patient by the central control system and/or a further medical examination performed under the control/instruction of the central control system.

The assessment results can be communicated to the server 18 and processed to determine the efficacy of the medication and/or the severity of the side effects experienced by the patient. Such data is used to determine an increase/decrease in repeat prescription dosage; a cessation of the medication, switch to alternative medication and/or cessation of the care program. Such data can additionally or alternatively be used to determine a suitable duration of the further prescription or a suitable interval until a further medical examination for the patient.

Once the time/date of receipt of a prescription is received, the control system can then schedule a medical examination in preparation for approval of a repeat prescription. The medical examination can be scheduled by the control system based on a suitable time period prior to the end of the initial prescription. As with the initial medical examination, each further medical examination is instructed by, and performed under the control of, the central control system. Communications indicating the proposed time/date and location for the medical examination can be transmitted to the relevant parties/devices, such as the physician and/or patient devices 34, 36 and the relevant confirmation or rescheduling replies are to confirm or rearrange the examination.

The further medical examination in some cases differs from the initial examination and comprises an examination of one or more patient organ, such as the heart or cardio-vascular function. Accordingly the equipment 32 used for the examination can comprise imaging/sonography equipment, such as echocardiography equipment for assessing structure and function of the heart. The results are collated, e.g. at equipment 32 or PC 34, according to a predetermined format prescribed by the central control system.

The results include one or more digital image of the heart and measurements associated therewith, such as dimensions of one or more internal structure of the heart and/or flow rate there-through.

In cases where test results are read and/or interpreted by a human operator, such as a physician, nurse, nurse practitioner technician or other trained medical worker, test results such as EKGs, ECGs, echocardiograms or other test results can be sent to a central or regional reading center to be read by experts having specialized or additional training or significant experience, such as a physician, specialist physician, a specially trained technician or a regional expert physician. The use of centralized facilities offers the advantages of improved consistency, quality and reliability of the evaluation.

The results are transmitted to the server 18, for storage in the patient database 22 along with the actual date/time of the examination. The results can be manually and/or automatically assessed by one or more algorithms or routines dictated by software on the central computer system. The predetermined format of the results allows comparison with prior examination results, so as to assess changes in patient health during care under the program. The algorithms can comprise one or more simple threshold for determining the suitability of the patient for ongoing prescriptions of the drug, such as fenfluramine. In certain cases, the algorithms can additionally or alternatively process/plot the medical examination data over time in order to determine a gradient, trend or other data feature in the results. Thus, algorithms can identify one or more patterns of patient response to the drug or other aspects of the care program and can categorize patient response to the care program, for example in terms of ongoing risk to patient health, and/or predict future patient wellbeing during the course of the program.

Such means of assessment of the patient response to the care program is beneficial in administering changes to the prescription for a particular patient. Furthermore the care program allows a means of ongoing research and development of the care program in response to patient outcomes. This is facilitated in a controlled manner, wherein the best prediction of patient outcome can be used at each repeat prescription stage. The prescribed data format is also highly desirable in that data between patients can be compared and statistical assessment can be performed on all the available variables to continuously update and improve the understanding of the impacts of different patient and treatment factors. As such, the central control of the care program represents a feedback and learning, whereby algorithms or models of patient response to the care program can be improved.

In the embodiment of issuance of a patient monitoring device 38 in addition to or instead of the further medical examination, the device is in some cases worn or routinely/repeatedly used or carried by the patient so as to allow ongoing monitoring of one or more indicator of patient wellbeing. In light of the above-discussed impact of fenfluramine or other epilepsy drugs on the cardio-vascular system, the patient monitoring device can monitor cardiovascular function. Dependent on the particular implementation of the invention, the patient monitoring device could be used to monitor patient seizures and output an alarm or other alert signal for acknowledgement by a carer. In such an embodiment, the carer can manually enter details of each noted seizure, e.g. into patient notes, a PC or other computing device for transmission to the central control system. Thus, the patient monitoring device can be a standalone device which does not itself communicate with the central control system. Varying levels of communication between the patient monitoring device and a local computing/communication device or else the central control system itself can be implemented in other embodiments of the invention.

In some embodiments, the patient monitoring device can be used to determine the number, regularity, duration and/or severity of seizures experienced by the patient during the course of treatment. In certain embodiments, the patient monitoring device can comprise one or more algorithm for determination of a type of seizure based on the sensor readings.

In certain instances, the patient monitoring device can be used to check/control correct administration of medication to/by the patient. The patient monitoring device can comprise a clock/timer and a user interface for entry of time at which a patient takes medication. The device can comprise one or more alarm or other alerting means to indicate an approaching or overdue time for taking medication according to a predetermined routine or elapsed time since a previous recorded medication.

In any such embodiments, the sensed/logged results from the patient monitoring device can be transmitted to the central control system for assessment and storage against the patient record. The device results can be processed by the device itself or by the central control system to data features and /or trends indicative of patient health or response to treatment under the care program.

The use a portable wearable device in monitoring epilepsy can be particularly beneficial in that epileptic seizures can be readily sensed/diagnosed and an corresponding alert signal can be sent in real time to any or any combination of the central control system, the patient's physician and or another care giver. For more damaging or prolonged seizures this alert signal can be crucial in ensuring timely care is provided to the patient.

In some examples, the patient monitoring device can be advantageously used to monitor compliance. The operational state of the patient monitoring device itself can also be monitored such that any error or abnormal operation of the device can be communicated to the patient, a carer or central control system. In the event of device malfunction, the central control system can schedule a medical examination of the patient prior to repeat prescription. In the manner described above the patient monitoring device can be used in combination with medical examinations in order to provide a more comprehensive, ongoing assessment of the patient or else can be used to reduce the frequency with which medical re-examinations are required.

The above described process of patient examination and/or monitoring can be repeated for each repeat prescription cycle. Thus, a history of use for each patient record is built up over time allowing the central control system to not only avoid significant patient risks that have been previously experienced but also repeat successful prescription regimes for each patient's individual requirements or else across a wider patient group.

Each change in prescription can be accompanied by transmission of information to the patient and/or carer/physician. As with the initial information, confirmation of receipt or approval can be required before the new prescription is authorized. In certain cases, a further database of care related documentation can be maintained, each item bearing an identifier, which identifiers can be logged in the patient database upon transmission to the patient/physician and/or approval received.

In combination with the central control of patient records and care program administration, the central control system allows for monitoring of drug inventory in the manner of a centralized pharmacy. Current inventory of the one or more drug used in the care program are maintained in the drug inventory database. Each time a prescription is authorized by the central control system and dispatched, the drug inventory database can be updated with the prescription details including the count/volume of the prescription, the dispatch date and the prescription identifier output by the control system.

The drug inventory database is updated with the confirmation of receipt communication received upon safe delivery of the prescription. Thus, the inventory database takes account of all currently held stock in the drug storage facility and all prescriptions in transit. Furthermore the drug inventory database can comprise a record of prescription duration such that the database can be interrogated to determine summary data of active prescriptions. This can be valuable to ensure restricted access to the patient database, such that personnel can access inventory reports and the like for stock control without the need to access patient's sensitive personal or medical data. Accordingly the inventory database 26 can be updated with non-sensitive data output by the patient database 2 and those databases can have different access restrictions. Updating of the inventory database can be at least partially automated, for example using conventional technology such as visual/printed codes or near field communication chips which can be scanned/interrogated at different stages of dispatch or delivery and/or upon receipt of data communications in accordance with the system described above.

In any embodiments, transmitted data by any one device can be encrypted or otherwise protected using conventional means to ensure data security.

The above described patient care program and associated control system thus can encompass each of: i) confirmation of diagnosis, ii) verifying compliance, iii) monitoring side effect profile and identifying failures in efficacy, in a manner not hitherto proposed in the prior art. Furthermore the genetic testing and/or medical examinations of the patient is paid for, co-ordinated and controlled by care program control system itself, i.e. by the drug company, thereby all of the test results can be correctly captured into the care program registry and fully utilized to improve patient care.

The comprehensive nature of the care program described above coordinates significant volumes of patient and program data which is beneficial not only in the immediate effective care of severe forms of epilepsy, such as Dravet Syndrome, but also in the longer term provision of a registry which can function as a research tool for epileptologists. This enables key opinion leaders and experts in different regions or countries to amass information and potentially collaborate in ongoing care improvement. Thus, whilst challenges have been overcome in the development and maintenance of a system in which such non-standardized information is logged, it has been found that the implementation of such a system can unlock significant potential in development of associated care programs.

Furthermore, the automation of many processes in the central control system can improve efficiency of drug distribution, for example by which refills of the drug are provided to the patient by the central pharmacy without the need for involvement by the prescribing physician.

Embodiments

Aspects of the present disclosure include a system for controlling distribution of a medication in the treatment or prevention of epilepsy. In some embodiments, the system comprises: a data storage facility including a database of patient records, each patient record having a medication authorization field; a central controller having one or more processors coupled to a communication network, which controls transmission and receipt of data via the network and which is coupled to the data storage facility to read and write data to the data storage facility; wherein the central controller outputs via the network an authorization of a first prescription of epilepsy medication to a patient in dependence upon genetic test results for the patient and schedules one or more subsequent test for the patient prior to authorization of one or more subsequent prescriptions of epilepsy medication.

In certain embodiments, the system further comprises a drug storage facility having at least one epilepsy medication stored therein. In certain embodiments, the system further comprises a drug storage facility having at least one epilepsy medication stored therein; wherein the central controller monitors drug inventory in the drug storage facility and controls dispatch of the medications from the drug storage facility to fulfil the first prescription and subsequent prescriptions. In certain embodiments, the system is for controlling distribution of medicaments in the treatment of refractory epilepsy. In certain embodiments, the central controller authorizes the first or further prescription comprising at least one of dosage, volume, count, regime, concentration and intended time period of use by the patient for a specified medication or active ingredient. In certain embodiments, the central controller instructs and/or coordinates the genetic test for the patient and the one or more subsequent tests for the patient. In certain embodiments, the central controller prescribes the data format for the test results, the data format being aligned with the patient test data fields and/or format of the database of patient records.

In certain embodiments, the central controller logs test results for one or more patients over time to generate a plot or trend in one or more test data fields. In certain embodiments, the central controller predicts future test results and/or categorizes patient test data by reference to one or more predetermined models. In certain embodiments, the one or more subsequent test comprises a physiological test for one or more patient organs. In certain embodiments, the subsequent test comprises echocardiography. In certain embodiments, the central controller outputs an initial or subsequent time period over which use of the medication by the patient is authorized and beyond which subsequent test results for the patient are required to be received before a following period of use for the patient is authorized. In certain embodiments, the central controller authorizes at least one of a repeat prescription, a change to the prescription and output of a proposal for cessation of the prescription dependent upon subsequent test results. In certain embodiments, the central controller monitors a patient monitoring device to collect data and analyses the data to determine response to treatment, and to determine occurrence of seizures and types of the seizures. In certain embodiments, the central controller acts as a centralized pharmacy for the medication and the patient database contains delivery address details for the patient, the central controller monitoring a confirmation of receipt of the medication at the delivery address.

In certain embodiments, the system further comprises a portable electronic device carried or worn by the patient for monitoring patient health, the electronic device comprising one or more sensors for measuring at least one of blood pressure, electrocardiography (ECG), heart rate, blood oxygen, temperature, and lung function. In certain embodiments, the electronic device is arranged to provide sensor readings in a format automatically processable by the central controller. In certain embodiments, an output from the electronic device is used by the central controller to determine at least one of a change to a scheduled medical test for the patient and a change to a medication prescription for the patient. In certain embodiments, the central data store comprises a database of authorized medical professionals, the central controller outputting authorization of one or more medical professionals upon completion of one or more data fields indicative of the reputation of the medical professional in the field of epilepsy. In certain embodiments, the system is for controlling distribution of medicaments in the treatment of Dravet Syndrome.

Aspects of the present disclosure include a method of controlling distribution of a medication in the treatment or prevention of epilepsy. In some embodiments, the method comprises: maintaining a central data storage facility including a database of patient records, each patient record comprising a medication authorization field, outputting from a central controller coupled to a communications network and to the data storage facility, an authorization of a first prescription of epilepsy medication to a patient over the communications network only in response to the results of a patient genetic test; scheduling by the central controller one or more subsequent tests for the patient prior to authorization of one or more subsequent prescriptions of epilepsy medication. In certain embodiments, the method further comprises monitoring by the central controller drug inventory in a drug storage facility and controlling dispatch of medications to fulfil prescriptions.

Aspects of the present disclosure include a data carrier comprising non-transitory machine readable storage media storing instructions for the control of one or more processors to function as a central controller of epilepsy medication by: controlling reading and writing of data to a central data storage facility including a database of patient records, each patient record comprising a medication authorization field; outputting from the central controller over a communications network an authorization of a first prescription of epilepsy medication to a patient only in response to the results of a genetic test for that patient being logged in the patient database; and automatically scheduling one or more subsequent tests for the patient prior to authorization of one or more subsequent prescriptions of epilepsy medication. In certain embodiments, the data carrier further comprises monitoring by the central controller of drug inventory in a drug storage facility and controlling dispatch of the medications to fulfil the prescriptions.

We claim:

1. A system for controlling distribution of a fenfluramine or pharmaceutical acceptable salt thereof for treating symptoms of a designated subtype of epilepsy, the system comprising:

a data storage facility comprising a database of patient records including address details for the patient, each patient record having a medication authorization field for entering a first prescription of fenfluramine or a pharmaceutically acceptable salt thereof;

a central controller having one or more processors coupled to a communication network, which central controller is coupled to the data storage facility to read and write data to the data storage facility via the network;

a drug storage facility having fenfluramine or a pharmaceutically acceptable salt thereof stored therein;

wherein the central controller of the system is programed to monitor drug inventory in the drug storage facility and further programed to control dispatch of fenfluramine or a pharmaceutically acceptable salt thereof from the drug storage facility; and wherein the central controller controls transmission and receipt of data to and from the data storage facility via the network, and acts as a centralized pharmacy for the medication, and confirms receipt of the fenfluramine or a pharmaceutically acceptable salt thereof at the patient address, the central controller being programed to output via the network a first authorization of a first prescription of fenfluramine or a pharmaceutically acceptable salt thereof to a specific patient previously subjected to a first echocardiographic imaging test, wherein output of the authorization is dependent upon the results of the first echocardiographic imaging test, and wherein the central controller is further programed to output a time period over which use of the fenfluramine or a pharmaceutically acceptable salt thereof by a patient is authorized and to schedule a subsequent echocardiograph imaging for the patient which subsequent test results for the patient are required to be received before authorizing additional fenfluramine or a pharmaceutically acceptable salt thereof for the patient, and further wherein the central controller is programmed to take an action dependent upon subsequent test results selected from authorizing an additional prescription, a change to the prescription and output of a proposal for cessation of the prescription.

2. The system according to claim 1, wherein the central controller is programed to authorize prescription related information regarding dosage, volume, count, regime, concentration and intended time period of use by the patient for fenfluramine or a pharmaceutically acceptable salt thereof; and further wherein the central controller coordinates subsequent tests for the patient.

3. The system according to claim 2, wherein the central controller is programmed to predict future test results and categorizes patient test data by reference to a predetermined model.

4. The system according to claim 1, wherein the central controller is programmed to prescribe a data format for test results for each patient, the data format being aligned with test data fields for each patient; and further wherein the central controller is programmed to log test results for each patient over time, and to generate a plot showing a trend for each patient.

5. The system according to claim 1, wherein the central controller is programmed to
monitor a patient monitoring device;
collect data related to patient treatment;
analyze the data collected;
determine patient response to treatment; and
determine occurrence of and type of seizures.

6. The system according to claim 1, further comprising:
a portable electronic device carried or worn by the patient for monitoring patient health, the electronic device comprising a sensor for measuring information selected from the group consisting of blood pressure, electrocardiography (ECG), heart rate, blood oxygen, temperature, and lung function, and
wherein the electronic device is arranged to provide sensor readings in a format compatible with the central controller.

7. The system according to claim 1,
wherein an output from an electronic device is used by the central controller to determine at least one of a change to a scheduled medical test for the patient and a change to a medication prescription for the patient; and further
wherein the central data storage facility comprises a database of authorized medical professionals, the central controller outputting authorization of one or more medical professionals upon completion of one or more data fields indicative of the reputation of the medical professional in the field of epilepsy.

8. The system according to claim 1, wherein the designated subtype of epilepsy is Dravet Syndrome.

9. A system for controlling distribution of a medication for treating symptoms of a designated subtype of epilepsy, the system comprising:

a data storage facility comprising a database of patient records including address details for the patient, each patient record having a medication authorization field for entering a first prescription of fenfluramine or a pharmaceutically acceptable salt thereof;

a central controller having one or more processors coupled to a communication network, which central controller is coupled to the data storage facility to read and write data to the data storage facility via the network; and wherein the central controller controls transmission and receipt of data to and from the data storage facility via the network, and acts as a centralized pharmacy for the medication, and confirms receipt of the fenfluramine or a pharmaceutically acceptable salt thereof at the patient address, the central controller being programmed to output via the network a first authorization of a first prescription of fenfluramine or a pharmaceutically acceptable salt thereof to a specific patient previously subjected to a first echocardiographic imaging test, wherein output of the authorization is dependent upon the results of the first echocardiographic imaging test, further programmed to schedule a subsequent medical test for the patient prior to allowing entry of a subsequent prescription for fenfluramine or a pharmaceutically acceptable salt thereof in the medication authorization field, wherein the subsequent medical tests is an echocardiographic imaging test, wherein the central controller is programed to output a time period over which use of the fenfluramine or a pharmaceutically acceptable salt thereof by a patient is authorized and beyond which subsequent test results for the patient are required to be received before authorizing additional fenfluramine or a pharmaceutically acceptable salt thereof for the patient, wherein the central controller is programmed to take an action dependent upon subsequent test results selected from authorizing an additional prescription, a change to the prescription and output of a proposal for cessation of the prescription, a drug storage facility having fenfluramine or a pharmaceutically acceptable salt thereof stored therein;

wherein the central controller of the system is programmed to monitor drug inventory in the drug storage facility and further programmed to control dispatch of fenfluramine or a pharmaceutically acceptable salt thereof from the drug storage facility, wherein the central controller is programed to authorize prescription related information regarding dosage, volume, count, regime, concentration and intended time period of use by the patient for fenfluramine or a pharmaceutically acceptable salt thereof;

wherein the central controller coordinates subsequent tests for the patient;

wherein the central controller is programmed to prescribe a data format for test results for each patient, the data format being aligned with test data fields for each patient; and further wherein the central controller is programmed to log test results for each patient over time, and to generate a plot showing a trend for each patient.

* * * * *